United States Patent [19]

Clements et al.

[11] 4,120,203

[45] Oct. 17, 1978

[54] CROSSCUT SAMPLER FOR PNEUMATIC CONVEYING SYSTEMS

[75] Inventors: George William Clements, Minneapolis; Hugo Wenshau, Burnsville, both of Minn.

[73] Assignee: Gustafson, Inc., Hopkins, Minn.

[21] Appl. No.: 787,369

[22] Filed: Apr. 14, 1977

[51] Int. Cl.² ............................................. G01N 1/20
[52] U.S. Cl. ................................. 73/422 R; 73/423 R
[58] Field of Search ............................ 73/422 R, 423 R

[56] References Cited

U.S. PATENT DOCUMENTS

| 3,279,260 | 10/1966 | Huntington | 73/423 R |
| 3,298,235 | 1/1967 | Platzer et al. | 73/423 R |

*Primary Examiner*—S. Clement Swisher
*Attorney, Agent, or Firm*—H. Dale Palmatier

[57] ABSTRACT

A crosscut sampler particularly useful for obtaining samples of flowing granular or particulate material in a pneumatic conveying system including a sample collecting head in a housing connected with the material conveying pipes, the head having a slot-shaped opening extending transversely across the flow passage of granular materials, there being a closure to seal the head and prevent entrance of materials between sampling cycles, the closure for the entrance to the head including a valve element within the head interior and movable into and out of obstructing relation with the entrance to the head, and an air cylinder on the head to operate the closure, the head being mounted on a slide for movement in the housing across the flow passage of flowing materials, and a collecting container to receive the samples from the head.

6 Claims, 5 Drawing Figures

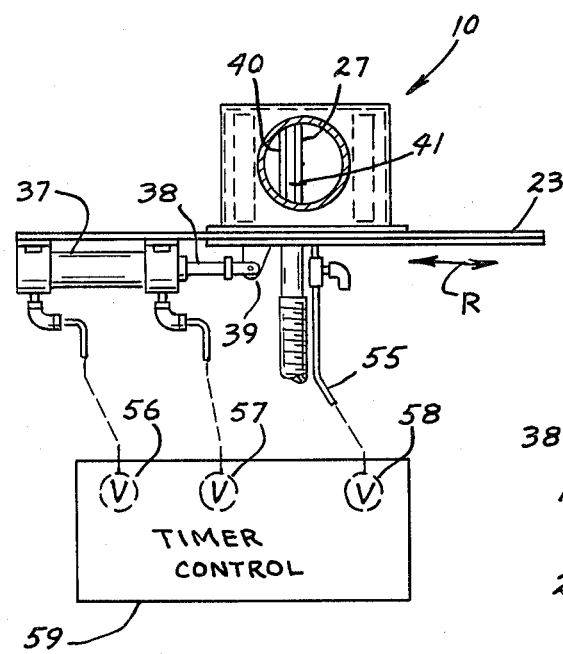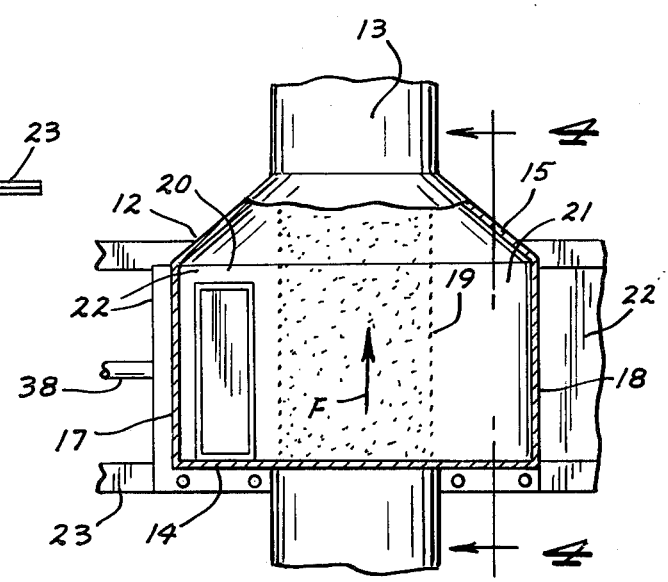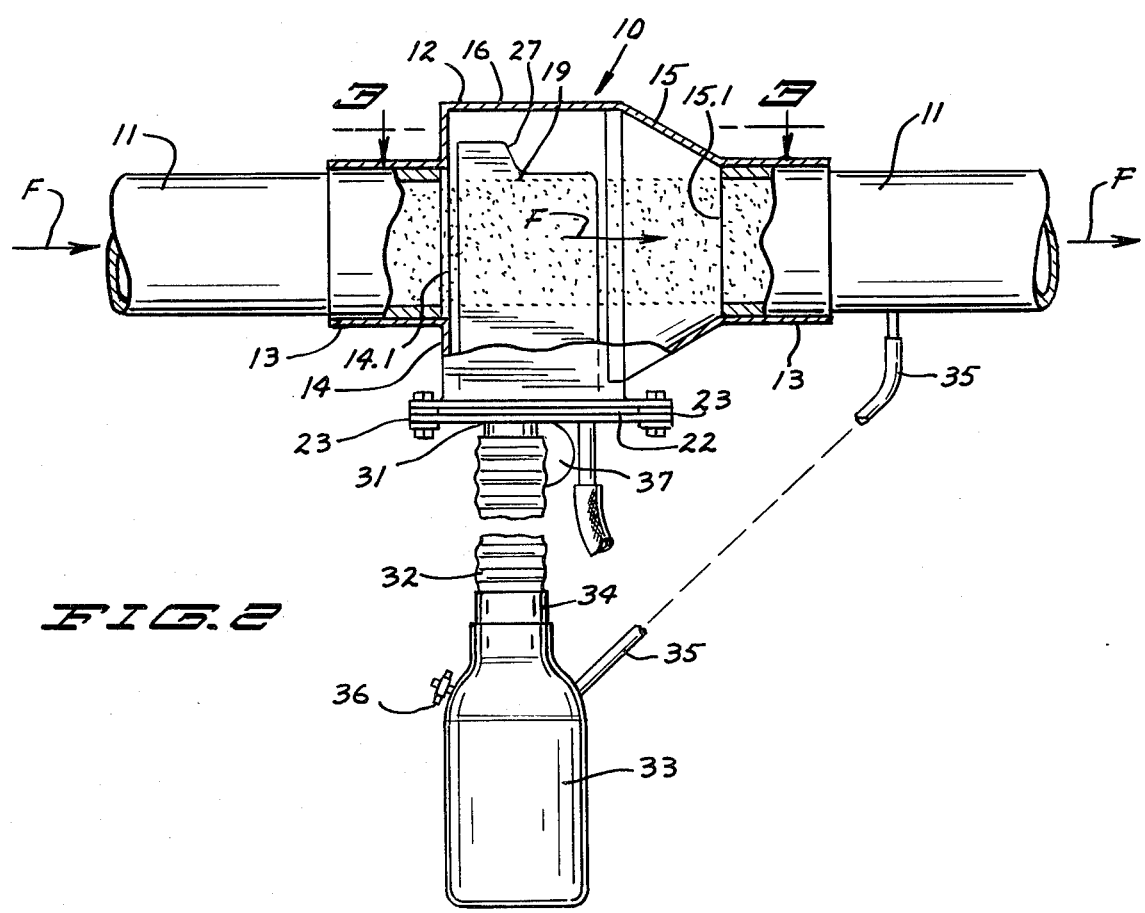

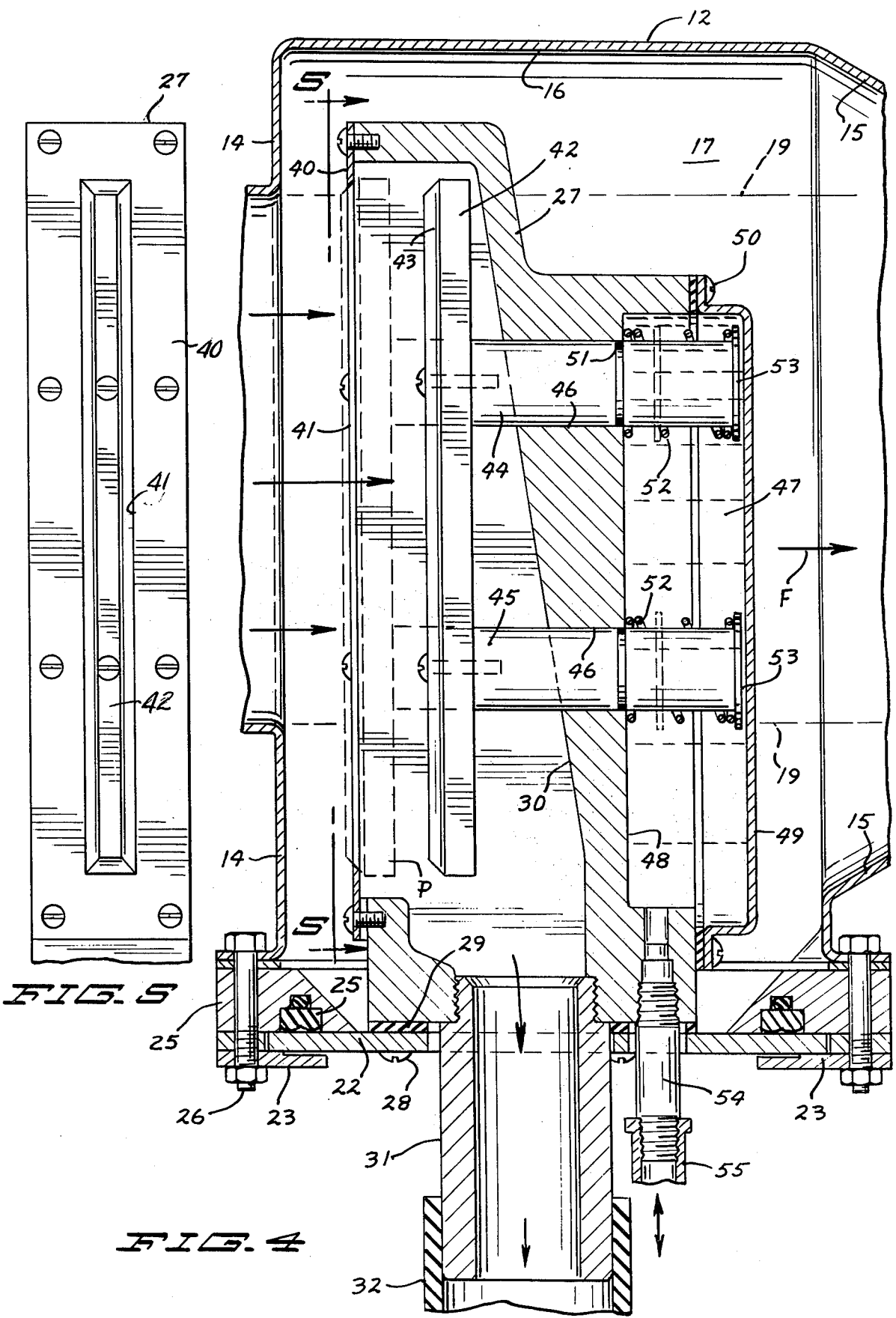

CROSSCUT SAMPLER FOR PNEUMATIC CONVEYING SYSTEMS

This invention relates to pneumatic conveying systems of the type used to convey particulate material which may be free flowing powder, granular or flake type material, and more particularly to apparatus for drawing representative samples of the material flowing in a pneumatic conveying system by taking a portion of the sample from every location in a plane lying transverse to the longitudinal flow of the material and the longitudinal orientation of the conveying pipe or tube.

BACKGROUND OF THE INVENTION

In pneumatic conveying systems, the particulate material being conveyed is essentially suspended in air which is caused to move through the conveying tubes at a rather high rate of speed. It is likely that in most pneumatic conveying systems, the particulate material being conveyed is not spread uniformly throughout the cross-sectional area of the conveying tube. Oftentimes there tends to be a concentration of the particulate material at a certain side of the tube; and in instances where the particulate material being conveyed comprises a mixture of two or more substances with different characteristics, the substances will not be spread uniformly across the cross-sectional area of the tube, but may be collected together at one side or another in the tube during the pneumatic conveying.

As a result, it is not possible to simply put a probe into the pneumatic conveying tube and extract a sample as has been done in the prior art because the sample is not likely to be truly representative of the material being conveyed in the system.

Particulate materials that are handled in a pneumatic conveying system tend to be somewhat dusty because oftentimes the particles are exceedingly small. Accordingly, sampling devices that have been used previously for sampling large granular materials such as feed grains, seed, etc., are not suitable for use in obtaining samples of the particulate material flowing in a pneumatic conveying system.

SUMMARY OF THE INVENTION

According to the present invention, the sampling station in the pipe of the pneumatic conveying system normally accommodates substantially free and unobstructed flow of the air and particulate material carried thereby in a direction along the conveying pipes or lines. The pneumatic system may be operating under partial vacuum or under superatmospheric pressure.

Normally the sample collecting head will be disposed off to the side of the stream of particulate laden air flowing through the sampling station. The sampling head is free to move in one direction entirely across the stream of particle laden air flowing along the conveying pipes; and the sampling head has a sample receiving slot which extends normal to the direction of movement of the head and sufficiently long as to extend entirely across the stream of flowing particle laden air. The sampling head may pass only once across the stream of flowing particle laden air in each sampling cycle, or it may be desirable that the sample collecting head be arranged to move across the stream and then back again to its original position in a single sampling cycle.

According to the present invention, it is significant that the sample receiving slot in the sampling head be entirely closed at the end of each sampling cycle and until the next sample is to be collected. The closure effected should sufficiently seal the slot and the sampling head against entry of dust or fine particles of particulate material in the periods of time between successive sampling cycles.

The present invention is also arranged as to minimize any likelihood of undesired collection of dust or particulate material in the vicinity of the sampling head during the time between sampling cycles so that substantially all of the particulate material will continue to flow along the conveying tubes in the pneumatic conveying system without interference.

As illustrated, the sampling head carries a closure element or valve to seat against the periphery of the sample receiving slot so that the slot can be opened and closed at the precise moment in the operating cycle as is desired. The closure for the sample receiving slot of the sampling head is operated by a suitable air operated control system and an air motor in the head.

In this sampling apparatus, it will be recognized that the sample collecting head is connected to a delivery duct which carries the collected samples away from the head. The duct extends transversely through one wall of the housing and is stationary with respect to that wall. The sampling head moves, in the housing, transversely through the flow passage for collecting samples of material, and the head should be recognized to move transversely of the direction of the delivery duct.

As a result, the delivery duct is entirely and continuously out of the central flow passage in the housing and the duct never interferes with the flow of material through the housing or with the collection of samples by the head.

In this instance, the transverse movement of the head is linear and is effected by mounting the head on a wall of the housing which comprises a slide and also carries the delivery duct.

BRIEF DESCRIPTION OF THE DRAWINGS

FIG. 1 is a schematic view of the sampling device and control apparatus therefor;

FIG. 2 is an enlarged elevation view partly in section of the sampling apparatus;

FIG. 3 is a detail section view taken at approximately 3—3 in FIG. 2;

FIG. 4 is an enlarged detail section view taken approximately at 4—4 in FIG. 3;

FIG. 5 is a detail elevation view of the front of the head as viewed at approximately 5—5 of FIG. 4.

DETAILED SPECIFICATION

One form of the invention is shown in the drawings and is described herein. The sampler is indicated in general by numeral 10 and is to be mounted in the conveying pipe or tube 11 of a pneumatic conveying system. Such systems may establish a subatmospheric pressure or partial vacuum in the pipe 11, or may establish a superatmospheric pressure in the conveying pipe. The particulate material which is conveyed through the pipe 11 is carried along by air. In the tube 11 illustrated in FIG. 2, the direction of flow of the particulate material is indicated by the letter F.

The sampler 10 has a closed and sealed housing 12 which is connected into the conveying pipe 11. The housing has tubular fittings 13 at its opposite ends which receive the ends of the pipes 11 therein and thereby support the housing 12 on the pipes which are ordinarily suspended securely on suitable supports.

The fittings or collars 13 are affixed as by welding to the housing 12 which also has a front wall 14 and a tapered rear wall 15. The housing also has a top wall 16 and opposite sidewalls 17 and 18.

The interior chamber of the housing is open and unobstructed and defines an unobstructed central flow passage between the aligned entrance and exit ports 14.1 and 15.1 in the front and rear walls 14 and 15, respectively. The unobstructed central flow passage is illustrated in FIGS. 2 and 3 and is indicated at 19 and it will be noted that the particulate material flowing through the pipes 11 and through the flow passage of the housing is indicated by stippling in these figures of the drawings. The flow passage 19 assumes the same cross-sectional configuration as the interior of the pipes 11, and because of the velocity and density of the material flowing in the pipes, will constitute a continuation of the flow from and to the pipes. It should also be noted that the housing is sufficiently wide as to define open portions or spaces 20 and 21 between the flow passage 19 and the opposite sidewalls 17 and 18, respectively.

The bottom wall 22 of the housing is defined by an elongate slide plate which is capable of reciprocation in the direction of arrows R indicated in FIGS. 1 and 2. The plate 22 is supported on a pair of elongate tracks 23 which underlie the housing 12 and extend transversely from the housing 12 in both directions. The housing has a sealing plate 24 extending around the periphery of the bottom of the housing, and carries resilient gaskets 25 in guideways thereon which will bear downwardly against the upper face of plate 22 to create an effective seal but still permit sliding of the plate on the track 23. The track 23 and the sealing frame 24 cooperatively define guideways for the edges of the plate 22 so as to adequately support, guide and seal the plate 22 relative to the housing; and the entire assembly is secured together as by bolts 26.

A sample collecting head 27 is affixed to the slidable plate 22 as by screws 28, and a sealing gasket 29 is provided between the bottom of the head 27 and the plate 22 to produce an air seal.

The width or thickness of head 27 is significantly less than the width of the central flow passage 19 in the housing and substantially less than the interior diameter of the pipes 11. The housing extends transversely across the housing and entirely transversely across the width of the unobstructed central flow passage in the housing.

The sample collecting head 27 has an interior chamber 30 into which the samples of particulate material are collected, and the interior chamber 30 is connected in flow communication with a delivery duct or tube 31 which protrudes transversely downwardly through the plate 22 and is threaded into the lower portion of the collecting head 27. The duct 31 also includes a flexible hose 32 which is detachably connected to a sample collecting jar 33. The jar 33 has a readily demountable fitting 34 for ready and easy disconnect from the hose or tube 32. An air transfer hose or tube 35 connects the interior of the jar 33 with the pipe 11 at a downstream location from the sampler 10 to equalize air pressure in the jar 33 with the air pressure in the pipe 11. The tube 35 is needed only when the pneumatic conveying system establishes a subatmospheric pressure or partial vacuum in the pipes 11; and in the instances when the pneumatic conveying system establishes a superatmospheric pressure in the pipes 11, the tube 35 is eliminated and the fittings capped, and a pet cock 36 is thereupon used to allow air pressure to escape from the bottle or jar 33 and an interior filter is used in connection with the pet cock to prevent escape of any particulate material.

An air cylinder 37 is mounted on the track 23 and the piston rod 38 thereof is connected to a drive bracket 39 affixed on the lower side of plate 22 in order to obtain the reciprocation of the plate to move the head 27 from the side portion 21 adjacent sidewall 18 of the housing, across the central flow passage 19, and into the other side portion 20 adjacent sidewall 17. It will be recognized that during the sliding movement of plate 22 and the movement of the head 27 across the flow passage, the delivery duct 31 does not at any time cross or interfere with the flow of particulate material through the unobstructed flow passage 19.

The head 27 is provided with a front face plate 40 in which an entrance slot 41 is formed. The entrance slot 41 is sufficiently long as to extend entirely across the width of the flow passage 19 in the housing so that particulate material from all portions of the flow passage will enter through the entrance slot 41 as the head 27 moves from side to side in the housing.

The front plate 40 is secured to the head as by screws. Immediately behind the front plate and in the interior chamber is a generally rigid closure 42 in the shape of a bar having beveled front corners 43 to fit into the slot 41 and entirely close the slot and produce an effective seal to prevent any undesired migration of dust or other small particles into the interior chamber of the head. The closure 42 is movable between the full line position illustrated in FIG. 4 and the dotted line position P thereof. The closure 42 is carried and moved by a pair of pistons 44 and 45 which are slidably mounted in a pair of bearing apertures 46 in the rear wall of housing 27, and the pistons extend into the rear chamber 47 which is formed by a recess 48 in the housing and a rear cover plate 49 which is affixed and sealed to the housing as by screws 50. The pistons 44 and 45 are sealed to the housing as by sealing rings 51, and are normally urged in a rearward direction, away from the plate 40 by coil springs 52 which bear at one end against the housing 27 and at the other end against a rigid ring or flange 53 on the end of each of the pistons 44 and 45. Air under pressure is delivered into and allowed to escape from the chamber 47 through a duct or tube 54 which is threaded into the lower portion of the housing so as to be in air flow communication with the chamber 47. A flexible hose 55 is connected to the tube or duct 54 for controlling the application of air pressure in the chamber 47.

A plurality of valves 56, 57 and 58 are respectively connected to the opposite ends of the air cylinder 37 and to the tube 55 for controlling the movement of the air cylinder and slide plate 22 and for producing closing of the slot 41 in the head 27.

The valves 56, 57 and 58 are operated by a suitable timer control mechanism 59 which may be programmed to move the head across the flow passage at the desired time and to cause the closure 42 to be moved out of the slot 41 whenever the head is moved from one side of the housing to another so that suitable samples of the flowing particulate material can be collected. When the head 27 has completed its pass through the central flow passage, and a suitable sample of the flowing material has been collected, the air pressure is applied into chamber 47 as to again cause the closure 42 to obstruct the slot 41 and produce a tight seal to prevent the entrance of any dust or small particles between the appropriate times at which samples are actually to be taken.

The closure 42 may be formed of a somewhat resilient material such as nylon, or may be a rigid steel piece with a resilient face at the beveled surfaces 43.

What is claimed is:

1. Apparatus for drawing a representative sample of flowing material from the conveying pipe of a pneumatic conveying system, comprising
   a sealed housing with aligned entrance and exit ports for connection into the conveying pipe, the housing having an open interior with an unobstructed central flow passage aligned with the ports to permit free flow of the material laden air moving through the pipe, the housing also having open side portions adjacent the central passage,
   means collecting and storing samples of the material flowing through the central passage of the housing and including a sample collecting head in the housing and movable therein from one side portion and in a first direction transversely of the central passage and entirely through said central passage and into another side portion, the head having a front face oriented to confront the entrance port of the housing and having an elongate opening to extend entirely across the central passage in a direction transversely of said first direction,
   means mounting and moving the collecting head in said first direction, and
   a closure in the housing and releasably engaging the head at the opening to tightly close and seal the opening, and the closure being on the head and movable into and out of obstructing relation with the opening.

2. Apparatus for drawing a representative sample of flowing material from the conveying pipe of a pneumatic conveying system, comprising
   a sealed housing with aligned entrance and exit ports for connection into the conveying pipe, the housing having an open interior with an unobstructed central flow passage aligned with the ports to permit free flow of the material laden air moving through the pipe, the housing also having open side portions adjacent the central passage,
   means collecting and storing samples of the material flowing through the central passage of the housing and including a sample collecting head in the housing and movable therein from one side portion and in a first direction transversely of the central passage and entirely through said central passage and into another side portion, the head having a front face oriented to confront the entrance port of the housing and having an elongate opening to extend entirely across the central passage in a direction transversely of said first direction,
   means mounting and moving the collecting head in said first direction, and
   a closure in the housing and releasably engaging the head at the opening to tightly close and seal the opening, and the closure being mounted within the head and being movable into and out of obstructing relation with the elongate opening to close the interior of the head.

3. Apparatus for drawing a representative sample of flowing material from the conveying pipe of a pneumatic conveying system, comprising
   a sealed housing with aligned entrance and exit ports for connection into the conveying pipe, the housing having an open interior with an unobstructed central flow passage aligned with the ports to permit free flow of the material laden air moving through the pipe, the housing also having open side portions adjacent the central passage,
   means collecting and storing samples of the material flowing through the central passage of the housing and including a sample collecting head in the housing and movable therein from one side portion and in a first direction transversely of the central passage and entirely through said central passage and into another side portion, the head having a front face oriented to confront the entrance port of the housing and having an elongate opening to extend entirely across the central passage in a direction transversely of said first direction,
   means mounting and moving the collecting head in said first direction, and
   a closure in the housing and releasably engaging the head at the opening to tightly close and seal the opening, and including a controllable means operable independently of head movement and moving the closure relative to the housing and relative to the head.

4. The apparatus according to claim 1 and including an air motor on the head and connected with and moving the closure.

5. The apparatus according to claim 3 and the closure being resiliently yieldable to closely conform to the head at the periphery of the opening.

6. The apparatus according to claim 4 and the head being elongate to traverse the entire central passage of the housing, an elongate face plate defining the elongate opening, the head having an open interior sample collecting chamber behind the face plate, the closure being elongate and disposed in the chamber in confronting relation to the face plate and the opening therein, the head also having a second elongate sealed pressure chamber extending along the sample chamber, means to convey air under pressure to the pressure chamber, and a pair of elongate slides affixed to the closure element and extending through the head into the pressure chamber and having piston-like faces in said pressure chamber against which pressurized air bears to move the slides and closure, and the slide having return means to move the slides and closure away from the face plate.

* * * * *

UNITED STATES PATENT AND TRADEMARK OFFICE
CERTIFICATE OF CORRECTION

PATENT NO. : 4,120,203
DATED : October 17, 1978
INVENTOR(S) : George William Clements and Hugo Wenshau It is certified that error appears in the above-identified patent and that said Letters Patent are hereby corrected as shown below:

In claim 5, line 1, delete "3" and substitute --2--.

Signed and Sealed this

Sixth Day of March 1979

[SEAL]

Attest:

RUTH C. MASON
*Attesting Officer*

DONALD W. BANNER
*Commissioner of Patents and Trademarks*